US010675313B2

(12) United States Patent
Perrier et al.

(10) Patent No.: US 10,675,313 B2
(45) Date of Patent: Jun. 9, 2020

(54) HAS2-STIMULATING PLANT EXTRACTS (75) Inventors: Eric Perrier, Les Cotes D'Arey (FR);
Anne Guezennec, Croissy sur Seine
(FR); Corinne Reymermier, Charly
(FR); Joelle Guesnet, Bures sur Yvette
(FR)

(73) Assignees: BASF Beauty Care Solutions France
(FR); Yves Saint Laurent Parfums
(FR)

( * ) Notice: Subject to any disclaimer, the term of this patent is extended or adjusted under 35 U.S.C. 154(b) by 348 days.

(21) Appl. No.: 11/600,517

(22) Filed: Nov. 16, 2006

(65) Prior Publication Data

US 2007/0184012 A1 Aug. 9, 2007

(30) Foreign Application Priority Data

Nov. 17, 2005 (FR) ..................... 05 11672

(51) Int. Cl.
| | |
|---|---|
| *A61K 36/185* | (2006.01) |
| *A61K 36/17* | (2006.01) |
| *A61K 36/896* | (2006.01) |
| *A61K 36/77* | (2006.01) |
| *A61K 36/605* | (2006.01) |
| *A61K 36/28* | (2006.01) |
| *A61K 36/38* | (2006.01) |
| *A61K 36/899* | (2006.01) |
| *A61K 36/48* | (2006.01) |

(52) U.S. Cl.
CPC ............ *A61K 36/185* (2013.01); *A61K 36/17* (2013.01); *A61K 36/28* (2013.01); *A61K 36/38* (2013.01); *A61K 36/48* (2013.01); *A61K 36/605* (2013.01); *A61K 36/77* (2013.01); *A61K 36/896* (2013.01); *A61K 36/899* (2013.01)

(58) Field of Classification Search
CPC .................................................. A61K 36/185
See application file for complete search history.

(56) References Cited

U.S. PATENT DOCUMENTS

| | | | |
|---|---|---|---|
| 6,184,199 B1 | 2/2001 | Pauly | 514/2 |
| 6,264,928 B1 | 7/2001 | Daniel et al. | |
| 6,403,108 B1* | 6/2002 | Abdullah | 424/401 |
| 6,566,405 B2* | 5/2003 | Weidner et al. | 514/733 |
| 6,579,543 B1 | 7/2003 | McClung | 424/728 |
| 8,734,865 B2 | 5/2014 | Choulot et al. | |
| 2002/0086906 A1* | 7/2002 | Weidner et al. | 514/733 |
| 2004/0146539 A1 | 7/2004 | Gupta | 424/401 |
| 2004/0175439 A1 | 9/2004 | Cyr | |
| 2005/0048008 A1 | 3/2005 | Gupta | 424/59 |
| 2005/0191267 A1 | 9/2005 | Luanratana | 424/74 |

FOREIGN PATENT DOCUMENTS

| | | | |
|---|---|---|---|
| DE | 29717497 U1 | 2/1999 | |
| DE | 10213480 A1 * | 10/2003 | |
| DE | 20122018 U1 | 12/2003 | |
| DE | 69815866 T2 | 5/2004 | |
| FR | 2 868 703 A1 | 10/2005 | |
| JP | 6009371 A | 1/1994 | |
| JP | 07017845 A * | 1/1995 | |
| JP | 11060467 A * | 3/1999 | |
| JP | 2000-247864 A | 9/2000 | |
| JP | 2000247830 A * | 9/2000 | |
| JP | 2002-128653 A | 5/2002 | |
| JP | 2003073288 A * | 3/2003 | |
| JP | 2004189644 A | 7/2004 | |
| JP | 2005002008 A * | 1/2005 | |
| JP | 2005-306779 A | 11/2005 | |
| JP | 2006-62987 A | 3/2006 | |
| KR | 2003005485 A * | 1/2003 | |
| KR | 20030005485 A * | 1/2003 | |
| KR | 2003-0084394 A | 11/2003 | |
| KR | 1020050010447 A | 1/2005 | |
| WO | 9833475 A1 | 8/1998 | |
| WO | 0015179 A2 | 3/2000 | |
| WO | WO 01/30313 A1 | 5/2001 | ............... A61K 7/48 |
| WO | 0241909 A1 | 5/2002 | |
| WO | WO 2004017934 A1 * | 3/2004 | |
| WO | WO 2004/078155 A1 | 9/2004 | ............... A61K 7/48 |

(Continued)

OTHER PUBLICATIONS

Ghusool from: Mohammad Ghani Khan. Najmul Qaraabaadeen Najm-al-Ghani (20th century AD), Munshi Nawal Kishore, Lucknow, (Second Edition) 1928 AD, p. 534. Retrieved from the Internet on: Nov. 11, 2011. Retrieved from the Internet: <URL: http://www.tkdl.res.in>.*
Jungermann et al. "Alternatives to Glycerine" from Glycerine: A Key Cosmetic Ingredient (1997). p. 411.*
Bilvadi Niruha Basti. From TKDL website. Retrieved from the Internet on: Dec. 27, 2017. From: Bhela Bhela Sa¼hit¢ English Translation,Commentary by K. H. Krishnamurthy; Edited by P. V. Sharma, Chaukhanbha Visvabharti, Varanasi, Edn. 1st 2000. pp. 565-566. (Year: 2000).*
Search Report from United Kingdom for Application No. GB0622032.1 dated Mar. 2, 2007.
English Abstracts of Application No. JP 2002-128653.
Search Report from France for Application No. FR0511672, dated Sep. 8, 2006.

(Continued)

Primary Examiner — Amy L Clark
(74) Attorney, Agent, or Firm — Faegre Drinker Biddle & Reath LLP (57) ABSTRACT The invention relates to plant extracts for stimulating the synthesis of hyaluronan synthase, particularly the synthesis of hyaluronan synthase 2 (HAS2). Specific aims of the invention are to increase firmness and/or elasticity and/or tissue moisturization, and/or increase the skin barrier effect, and/or increase tissue resilience, and/or modulate angiogenesis, or the neocreation of blood capillaries, and/or improve healing, and/or cell proliferation, migration or differentiation, and/or skin atrophy, and/or intended to combat the effects of ageing on the skin, and in particular to combat the loss of firmness of the skin observed in the course of ageing, and/or atrophied scars.

12 Claims, 4 Drawing Sheets

(56) References Cited

FOREIGN PATENT DOCUMENTS

| WO | WO-2005/034891 A2 | 4/2005 | |
|----|-------------------|--------|--|
| WO | WO 2005/035548 A1 | 4/2005 | ............ C07H 21/04 |
| WO | 2005102259 A1 | 11/2005 | |
| WO | WO 2006/070978 | 7/2006 | ............ A61P 17/16 |

OTHER PUBLICATIONS

Patent Abstracts of Japan, abstracting JP 2003-040758.
Derwent Abstract No. 2004-464201 abstracting JP 2004-168732.
Derwent Abstract No. 2003-817827 abstracting JP 2003-128569.
Derwent Abstract No. 2001-605341 abstracting JP 2001-192338.
Derwent Abstract No. 2001-227311 abstracting CN 1277839.
Derwent Abstract No. 2003-861742 abstracting KR 2003-057205.
Aug. 25, 2008 Spanish Search Report Performed.
Centerchem, Inc., "Soothing/Anti-Inflammation/Sensitive Skin", www.centerchem.com, Jul. 14, 2009.
Office Action issued in Korean Application No. 10-2014-0017966 dated Jul. 13, 2016 with English Translation Attached.

\* cited by examiner

HAS2-STIMULATING PLANT EXTRACTS

This application claims priority from French patent application serial number 0511672, filed Nov. 17, 2005.

The invention relates to cosmetic and pharmaceutical compositions comprising plant extracts, in particular for obtaining a firming effect of the skin, especially of the dermis, subsequent to stimulation of the HAS protein.

BACKGROUND

The extracellular matrix consists of a complex network of varied molecules of protein or carbohydrate origin, that are responsible for an environment favorable to correct cellular functioning.

During cellular events such as proliferation, migration or differentiation, the extracellular matrix modifies and adapts. In the polysaccharide family, glycosaminoglycans (GAGs), and among these hyaluronic acid (HA), are key structural components of this extracellular matrix. These GAGs, which have very high molecular weights, possess many physiological functions, such as moisturizing tissues, increasing the skin barrier effect, and promoting the resilience and elasticity of tissues by virtue of their ability to trap water. Moreover, they have been described in the modulation of angiogenesis or neocreation of blood capillaries, of healing, of proliferation, of migration and of cell differentiation by means of membrane receptors such as CD44 and RHAMMs (receptor for hyaluronan mediated motility) located at the cell surface (Lesley J. et al., J. Exp. Med., 175, 257-266 (1992); Peck D. et al., Journal of Cell Science, 111, 1595-1601 (1998); Assmann V. et al., Journal of Cell Science, 111, 1685-1694 (1998)).

Moreover, the presence of hyaluronic acid at the dermal-epidermal interface is thought to make it possible to facilitate metabolic exchanges between the two tissues. Finally, hyaluronic acid also allows associations with other molecules such as versican, fibrinogen and collagens type I and VI (Mc Devitt et al., FEBS Lett., 3, 294, 167-170 (1991); Le Baron et al., J. Biol. Chem., 14, 267, 10003-10010 (1992)).

Hyaluronic acid, which has been more thoroughly studied than the other GAGs, is like a linear polysaccharide composed of repeating disaccharide units: N-acetyl-D-glucosamine-$\beta(1\rightarrow4)$-D-glucuronic acid $\beta(1\rightarrow3)$. It is synthesized on the inner side of the plasma membrane by successive additions of UDP-N-acetylglucosamine and of UDP-D-glucuronic acid combined via $\beta(1\rightarrow4)$ and $\beta(1\rightarrow3)$ linkages, and then secreted directly into the extracellular space (Weigel et al., J. Biol. Chem., 272, 13997-14000 (1997)). This synthesis is carried out by monomeric membrane-bound enzymes called hyaluronan synthases (HASs), identified as three isoforms in vertebrates: HAS1, HAS2 and HAS3 (Weigel et al., J. Biol. Chem., 272, 13997-14000 (1997)) transcribed from 3 distinct genes located on various chromosomes. More particularly, the gene encoding the HAS2 protein is located on chromosome 8 and is sensitive to the presence of various growth factors such as PDGF-BB, TGF-$\beta$1, EGF or else FGF and KGF.

GAGs are found in approximately all tissues and their amounts in the extracellular matrix are greatly modified under certain conditions such as skin atrophy, age, atrophy scars, and probably osteoporosis. The skin, and more particularly the dermis, contains approximately 50% of the total amount of hyaluronic acid present in an organism (Laurent et al., FASEB J., 6, 2397-2404 (1992)) and studies have shown a strong cause-effect relationship with respect to age, with a complete absence of hyaluronic acid synthesis after 60 years of age (Ghersetich et al., Int. J. Dermatol., 33, 119-122 (1994)). This hyaluronic acid is synthesized by the HASs of dermal fibroblasts.

At the epidermal level, hyaluronic acid is synthesized by keratinocyte HASs and plays a role in the migration, proliferation and differentiation thereof. The decrease in hyaluronic acid leads to a thinning of the epidermis which can be attributed to the acceleration of keratinocyte terminal differentiation.

For cosmetic or dermopharmaceutical applications, a certain number of compounds have been studied for their ability to stimulate, in keratinocytes, the production of glycosaminoglycans in general, and of hyaluronic acid in particular.

After having demonstrated that HAS2 can be induced by various substances such as TNF-alpha, interferon-gamma, interleukin-1 beta (Ijuin et al. 2001, Arch. Oral Biol. 46(8): 767-72), various teams have attempted to stimulate HAS2 production with substances such as retinoic acid, on a model of keratinocytes in culture, in order to evaluate the effects on the quality and the structure of the epidermis of skin from normal volunteers thus treated. The conclusion of these studies is that all the pro-inflammatory cytokines stimulate the production of HAS2 and therefore of hyaluronan in cells in culture (Jacobson A, Brinck J, Briskin M J, Spicer A P and Heldin P. 2000. Expression of human hyaluronan synthases in response to external stimuli. Biochem. J. 348(Pt 1): 29-35). Thus, substances such as retinoic acid, recently, ginseng substance K (or 20 O-beta-D glucopyranosyl 20 S protopanaxadiol) has recently been described as being capable of stimulating HAS2 synthesis in transformed keratinocyte-type HaCat cells or in human fibroblasts in culture (Kim et al., IFSCC Magazine 7(3), 189-196 (2004)).

SUMMARY OF THE INVENTION

One aim of the invention is to provide compounds, particularly compounds extracted from plants, that can be used topically for stimulating the expression and/or the activity of HAS2, in order to increase the amount of glycosaminoglycans and of hyaluronic acid in the skin, and in particular in the dermis, and to thus increase the firmness of the skin.

Another aim of the invention is especially to provide the compounds mentioned above, for improving, in the skin, firmness and/or elasticity and/or tissue moisturization, and/or increasing the skin barrier effect, and/or increasing tissue resilience, and/or modulating angiogenesis, or the neocreation of blood capillaries, and/or improving healing, or cell proliferation, migration or differentiation.

In particular, one aim of the invention is to provide the compounds mentioned above, for combating skin atrophy, in particular combating dermal atrophy, the effects of ageing on the skin, atrophied scars, or the loss of firmness of the skin observed in the course of ageing.

DETAILED DESCRIPTION OF THE INVENTION

The present invention describes, in a first aspect, the use of an effective amount of at least one plant extract as an active ingredient for stimulating the expression and/or the activity of hyaluronan synthase, and in particular stimulating the expression and/or the activity of hyaluronan synthase 2 (HAS2), in a cosmetic composition. The term "effective amount" as used herein means an amount of the extract sufficient to significantly induce a positive benefit, including independently or in combinations, the benefits disclosed herein.

The invention describes, according to a second aspect, the use of an effective amount of at least one plant extract as an active ingredient for stimulating the expression and/or the activity of hyaluronan synthase, and in particular stimulating the expression and/or the activity of hyaluronan synthase 2 (HAS2), for producing a pharmaceutical, and especially dermopharmaceutical, composition.

The inventors mean by "stimulating the expression of hyaluronan synthase (HAS, in particular of HAS2)", in particular the stimulation of the synthesis of hyaluronan synthase (HAS, in particular HAS2).

In particular, the active ingredients according to the present invention make it possible to obtain stimulation of the expression of the gene encoding the HAS2 protein in fibroblasts, in particular in human fibroblasts, and especially in human cutaneous tissues such as the dermis.

Advantageously, the active ingredients make it possible to increase the firmness and/or the elasticity of the cutaneous tissues, in particular of the dermis.

Advantageously, the active ingredients make it possible to increase the production and/or the amount of glycosaminoglycans in general, and of hyaluronic acid in particular, especially in the dermis.

Advantageously, the active ingredients according to the present invention do not substantially induce any inflammatory reaction in the skin, and are therefore compatible with topical application, particularly cosmetic or dermopharmaceutical applications. The term "topical application", as used herein, means to apply or spread the compositions of the present invention onto the surface of skin tissue.

Advantageously, the composition is intended to improve, in the skin, firmness and/or elasticity and/or tissue moisturization, and/or increase the skin barrier effect, and/or increase tissue resilience, and/or modulate angiogenesis, or the neocreation of blood capillaries, and/or improve healing, and/or cell proliferation, migration or differentiation, and/or skin atrophy, and/or intended to combat the effects of ageing on the skin, and in particular to combat the loss of firmness of the skin observed in the course of ageing, and/or atrophied scars and/or the cutaneous tissue atrophy observed in the course of ageing, in particular to combat dermal atrophy.

Advantageously, the compounds according to the present invention are used for combating the thinning of cutaneous tissues, and in particular of the skin.

Advantageously, the compounds used according to the present invention are plant extracts. In particular, the active ingredient may be an extract of a plant chosen from the following: Guarana (*Paullinia cupana*), St. John's wort (*Hypericum hircinum*), bamboo (*Bambusa vulgaris*), mung (*Phaseolus aureus*), gooseberry (*Ribes uva-crispa* L.), bean (*Phaseolus aureus*), gooseberry (*Ribes uva-crispa* L.), butcher's broom (*Ruscus aculeatus*), broad bean (*Vicia faba equina*), pea (*Pisum sativum*), lupin (*lupinus angustifolius*), Ephedra (*Ephedra sinica*), tansy (*Tanacetum vulgare*), Indian shell flower (*Alpinia galanga*), white mulberry (*Morus alba*), J'oublie (*Pentadiplandra brazzeana*), or a mixture of such extracts.

Preferably, the active ingredient is a plant extract chosen from an extract of white mulberry (*Morus alba*), an extract of Ephedra (*Ephedra sinica*), an extract of Guarana (*Paullinia cupana*), an extract of tansy (*Tanacetum vulgare*), an extract of Indian shell flower (*Alpinia galanga*), an extract of J'oublie (*Pentadiplandra brazzeana*), or a mixture of such extracts.

Advantageously, the compounds according to the present invention are used for increasing the firmness and/or the elasticity of cutaneous tissues, in particular of the dermis.

A polar solvent or a mixture of polar solvents is advantageously used to obtain said extract. Among the usual extraction solvents, use may be made of a protic solvent chosen from the group consisting of: water, methanol, ethanol, propanol, butanol, pentanol, cyclohexanol, diethylene glycol, HO—$(CH_2)_2$—OH, and a mixture thereof. Use may also be made of a polar aprotic solvent, in particular chosen from the group consisting of: pyridine, butanone, acetone, $Ac_2O$, $(Me_2N)_2CO$, PhCN, $CH_3CH_2CN$, HMPA, $PhNO_2$, $MeNO_2$, DMF, MeCN, sulpholane, DMSO, $HCONH_2$, HCONHMe, $CH_3CONHMe$, and a mixture thereof. Water, an alcohol such as ethanol, propanol, isopropanol or butanol, a polyol such as butylene glycol, or an ester such as ethyl acetate, or a mixture of these solvents, is preferably used. The proportions of the mixtures of the solvents mentioned above generally range between 1:1 and 1:100, and preferably between 1:1 and 1:10; a 25/75 mixture is, for example, used.

The extraction can be carried out with agitation and/or heating, for A example to between 30° C. and 60° C., or to the reflux of the solvent used. The extraction is usually carried out at atmospheric pressure, but an extraction under pressure can be used. The extraction time is assessed by those skilled in the art, and depends in particular on the extraction conditions. Advantageously, several extractions are carried out. The fractions obtained can in particular be combined if desired.

Advantageously, the extracts obtained are filtered and then optionally concentrated and/or evaporated until the desired quality of dry products is obtained.

The compounds according to the present invention are prepared in the form of topical compositions, in particular of cosmetic, dermopharmaceutical or pharmaceutical compositions. As a result, for these compositions, the excipient contains, for example, at least one compound chosen from the group consisting of preserving agents, emollients, emulsifiers, surfactants, moisturizers, thickeners, conditioners, matifying agents, stabilizers, antioxidants, texturing agents, sheen agents, film-forming agents, solubilizing agents, pigments, dyes, fragrances and sunscreens. These excipients are preferably chosen from the group consisting of amino acids and derivatives thereof, polyglycerols, esters, cellulose polymers and derivatives, lanolin derivatives, phospholipids, lactoferrins, lactoperoxidases, sucrose-based stabilizers, vitamin E and its derivatives, natural and synthetic waxes, plant oils, triglycerides, unsaponifiable products, phytosterols, plant esters, silicones and derivatives thereof, protein hydrolysates, jojoba oil and its derivatives, liposoluble/water-soluble esters, betaines, amino oxides, plant extracts, sucrose esters, titanium dioxides, glycines and parabens, and also preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerol, sodium dihydroxycetyl, isopropyl hydroxycetyl ether, glycol stearate, triisononaoin, octyl cocoate, polyacrylamide, isoparaffin, laureth-7, a carbomer, propylene glycol, glycerol, bisabolol, a dimethicone, sodium hydroxide, PEG-30 dipolyhydroxystearate, capric/caprylic triglycerides, cetearyl octanoate, dibutyl adipate, grapeseed oil, jojoba oil, magnesium sulphate, EDTA, a cyclomethicone, xanthan gum, citric acid, sodium lauryl sulphate, mineral oils and waxes, isostearyl isostearate, propylene glycol dipelargonate, propylene glycol isostearate, PEG-8 beeswax, hydrogenated heart-of-palm oil glycerides, hydrogenated palm oil glycerides, lanolin oil, sesame oil, cetyl lactate, lanolin alcohol, castor oil, titanium dioxide, lactose, sucrose, low-density polyethylene, and an isotonic salt solution.

Advantageously, the abovementioned compositions are formulated in a form chosen from the group consisting of an aqueous or oily solution, a cream or an aqueous gel or oily gel, in particular in a jar or in a tube, in particular a shower gel, a shampoo; a milk; an emulsion, a microemulsion or a nanoemulsion, in particular oil-in-water or water-in-oil or multiple or silicone-based; a lotion, in particular in a glass or plastic bottle or in a metering bottle or in an aerosol; and ampoule; a serum; a liquid soap; a dermatological cleansing bar; an ointment; a mousse; an anhydrous, preferably liquid, pasty or solid, product, for example in the form of a stick, in particular in the form of a lipstick.

The amounts of said active ingredient normally used range between 0.001% and 20% by weight of the total composition, preferably between 0.001% and 10% by weight, and between 0.01% and 10% by weight of the total composition are even more preferably used.

The compounds described above can optionally be combined with another active ingredient so as to obtain an improved effect. Preferably, as the composition is to be in contact with human skin tissue, any additional components and active ingredients should be suitable for application to such tissue; that is, when incorporated into the composition they are suitable for use in contact with human skin tissue without undue toxicity, incompatibility, instability, allergic response, and the like within the scope of sound medical judgment. The CTFA Cosmetic Ingredient Handbook, Eleventh Edition (2006) describes a wide variety of nonlimiting cosmetic and pharmaceutical ingredients commonly used in the skin care industry, which are suitable for use in the topical compositions of the present invention. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

According to another aspect, the invention relates to a cosmetic care process comprising the use of the compositions mentioned above.

According to another aspect, the invention relates to a pharmaceutical treatment process, in particular a dermopharmaceutical treatment process, comprising the use of the compositions mentioned above, and comprising in particular the administration of an effective amount of at least one active ingredient mentioned above to an individual having need thereof.

The application mentioned above can be carried out once or several times a day, in particular by topical application.

Other aims, characteristics and advantages of the invention will emerge more clearly to those skilled in the art subsequent to reading the explanatory description that refers to examples which are given only by way of illustration and which can in no way limit the scope of the invention.

The examples are an integral part of the present invention and any characteristic appearing to be novel with respect to any prior state of the art based on the description taken as a whole, including the examples, is an integral part of the invention in its function and in its generality. Thus, each example has a general scope.

Furthermore, in the examples, all the percentages are given by weight, unless otherwise indicated, and the temperature is expressed in degrees Celsius unless otherwise indicated, and the pressure is atmospheric pressure, unless otherwise indicated.

EXAMPLES

Example 1: Stimulation of the Expression of the Gene Encoding the HAS2 Protein (A) Normal human fibroblasts are obtained after collagenase extraction from abdominal biopsies derived from surgical resection.

The fibroblasts are amplified in Fibroblast Culture Medium (FCM) composed of Dulbecco's Modified Eagle's Medium (DMEM glutamine stabilized, Invitrogen) supplemented with 10% of calf serum (Hyclone), 25 mg/l of gentamycin, 100 000 IU/l of penicillin, 1 mg/l of amphotericin B and 50 mg/l of sodium ascorbate (Sigma). 1.5 ml of FCM are distributed per well and the culture is carried out at 37° C. under 5% $CO_2$. The medium is replaced three times a week. The fibroblasts are then seeded at 10 000 cells per $cm^2$ into 24-well plates in 1 ml of Fibroblast Basal Medium (Promocell) and amplified until confluency.

(B) The active agents (tested for the screening method at the concentration of 1%) are diluted in the culture medium depleted of antibiotics, antifungal agents and growth factors. The expression of the gene is detected by real-time RT-PCR by measuring the expression of each gene in relation to actin (housekeeping gene) and expressed as % of the nontreated negative control. 10 µl of 5 ng/µl total RNA i-are added to 40 µl of PCR mix (composed of 25 µl of 2×SYBR Green Buffer Mix, 0.5 µl of enzyme mix, 0.5 µM, final concentration, of sense primer and 0.5 µM, final concentration, of antisense primer, and water qs 40 µl). The RT-PCR takes place in various steps, including reverse transcription at 50° C., 30 min, polymerase activation at 95° C., 15 min, and performing of PCR cycles (95° C., 15 s; hybridization temperature specific to each gene/30 s; 72° C./30 s)×50 cycles. The sense and antisense oligonucleotides are, respectively, CGAGTTTACTTCCCGCCAAGA and CTTCCGC-CTGCCACACTTATTGAT, and the hybridization temperature is 56° C.

Out of all the products evaluated, the products below give satisfactory results since they stimulate the production of mRNA encoding HAS2. These products can therefore be used in cosmetics for stimulating HAS2 synthesis in the dermis, and inducing firmness of the skin.

Preferably, an extract is prepared from a part of the plant cut up at 10% (w/w) in water, or ethanol, optionally at reflux. The extraction is carried out for 1 hour, the solution is then filtered, the ethanol is eliminated, and the product obtained is solubilized at 5% (w/w) in a water/glycol mixture and then ultrafiltered through a ceramic filter having various cut-off thresholds, and, finally, filtered at 0.45 µm. Ethanol, ethyl acetate, DMSO, acetone or a mixture of 75% water and 25% butylene glycol can also be used as solvent instead of water. The preferred extraction types are those indicated in Table 1.

Example 2: Dose-effect Validation of the Effects Obtained with One of the Ingredients Selected (Extract of White Mulberry-JVEG022A)

Fibroblast cultures are prepared as indicated in Example 1 and are incubated in the presence of increasing amounts of

TABLE 1

| Reference of the selected products | Latin name of the plant | Part of the plant used | Extraction type | STIMULATION of HAS2 mRNA relative to basal level |
|---|---|---|---|---|
| JVEG056A | (Guarana) *Paullinia cupana* | Whole seed | Aqueous fraction | ×4 |
| JVEG057A | (St John's wort) *Hypericum hircinum* | Whole plant | Aqueous fraction | ×3 |
| JVEG073N | (Bamboo) *Bambusa vulgaris* | Stems | Aqueous fraction | ×4 |
| JVEG261A | (Mung bean) *Phaseolus aureus* | Germinated seeds | Aqueous fraction | ×2 |
| JVEG368A | (Gooseberry) *Ribes uva-crispa* | Fruit | Aqueous fraction | ×2 |
| JVEG418A | (Butcher's broom) *Ruscus aculeatus* | Root | Aqueous fraction | ×7.5 |
| JPRO060A | (Broad bean) *Vicia faba equina* | Whole seeds | Aqueous fraction | ×4 |
| JPRO065A | (Pea) *Pisum sativum* | Whole seeds | Aqueous fraction | ×2 |
| JPRO057A | (Lupin) *Lupinus angustifolius* | Whole seeds | Aqueous fraction | ×2 |
| JPRO019A | (Lupin) *Lupinus angustifolius* | Modified lupin seed proteins | Aqueous fraction | ×4 |
| JVEG166A | (Ephedra) *Ephedra sinica* | Plant | Aqueous fraction | ×9 |
| JVEG681A | (Tansy) *Tanacetum vulgare* | Flowers | Aqueous fraction | ×2.6 |
| JVEG 203A | (Indian shell flower) *Alpinia galanga* | Roots or leaves | Aqueous fraction | ×1.8 |
| JVEG022A | (White mulberry) *Morus alba* | Root | Aqueous fraction | ×17 |
| JVEG060A | *Pentadiplandra Brazzeana* | Root | Aqueous fraction | ×2 |

It is thus preferred to carry out an extraction, preferably with a polar solvent or a mixture of polar solvents, optionally at reflux, preferably of the part of the plant mentioned in Table 1. Once the extraction has been carried out, the solution is filtered and optionally resolubilized in a space polar solvent or a mixture of polar solvents. Prior to the extraction, the part(s) of the plant used can advantageously be ground.

Figure 1:
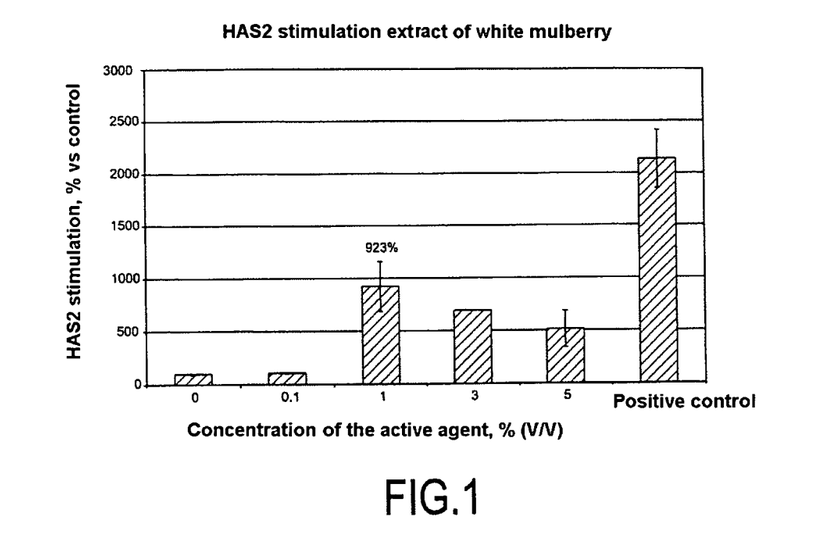
FIG. 1 is a graphical representation of the HAS2 stimulation with an extract of white mulberry.

It is advantageous to obtain an extract of the plants used as starting material, using a solvent, preferably a polar solvent, and preferably water, a mixture of water/alcohol or polyol, for instance a water/glycol or water/ethanol mixture, or a polyol, or an alcohol such as ethanol. The extract is preferably filtered and then dried. It is also possible to carry out the extraction with moderate heating, for instance at 45° C. or at reflux. The extraction is preferably carried out with agitation. The extraction methods are well known to those skilled in the art. The part of the plants used can vary as a function of the extract to be obtained.

the extract selected. After mRNA extraction, the amounts of mRNA encoding HAS2 are detected using Q-RT-PCR as described in Example 1. The results are given as percentage activation as a function of the nontreated cell culture used as a study control, and are given in FIG. 1. A significant dose-effect is observed for this active agent, which means that its activity must be relatively specific. When used at 1%, this extract makes it possible to obtain a more than 900% stimulation of HAS2 mRNA, which represents a very positive and very significant result.

Example 3: Dose-effect Validation of the Effects Obtained with One of the Ingredients Selected (Extract of *Ephedra*-JVEG166A)

Figure 2:
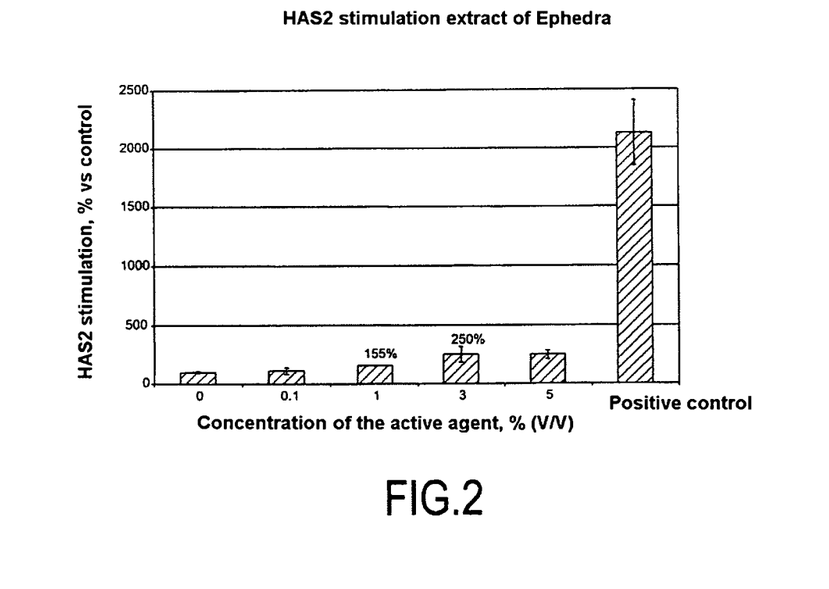
FIG. 2 is a graphical representation of the HAS2 stimulation with an extract of *Ephedra*.

Fibroblast cultures are prepared as indicated in Example 1 and are incubated in the presence of increasing amounts of the extract selected (extract of *Ephedra*). After mRNA extraction, the amounts of mRNA encoding HAS2 are detected using Q-RT-PCR as described in Example 1. The results are given as percentage activation as a function of the nontreated cell culture used as a study control, and are given in FIG. 2. A significant dose-effect is observed for this active agent, which means that its activity must be relatively specific. When used at 1%, this extract makes it possible to obtain a 155% stimulation of HAS2 mRNA, which represents a very positive result.

Example 4: Dose-effect Validation of the Effects Obtained with One of the Ingredients Selected (Extract of Guarana-JVEG056A)

Figure 3:
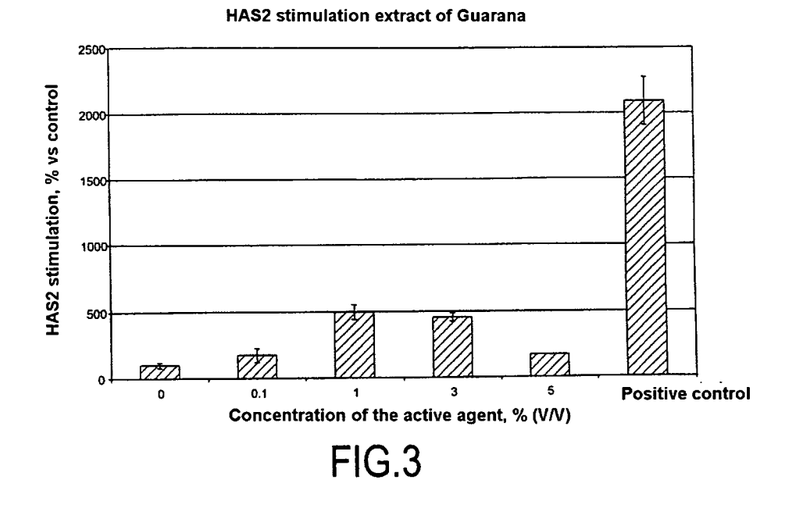
FIG. 3 is a graphical representation of the HAS2 stimulation with an extract of *Guarana*.

Fibroblast cultures are prepared as indicated in Example 1 and are incubated in the presence of increasing amounts of the extract selected (extract of *Guarana*). After mRNA extraction, the amounts of mRNA encoding HAS2 are detected using Q-RT-PCR as described in Example 1. The results are given as percentage activation as a function of the nontreated cell culture, used as a study control, and are given in FIG. 3. A significant dose-effect is observed for this active agent, which means that its activity must be relatively specific. When used at 1%, this extract makes it possible to obtain a 500% stimulation of HAS2 mRNA, which represents a very positive result.

Example 5: Dose-Effect Validation of the Effects Obtained with One of the Ingredients Selected (Extract of Tansy-JVEG681A)

Figure 4:
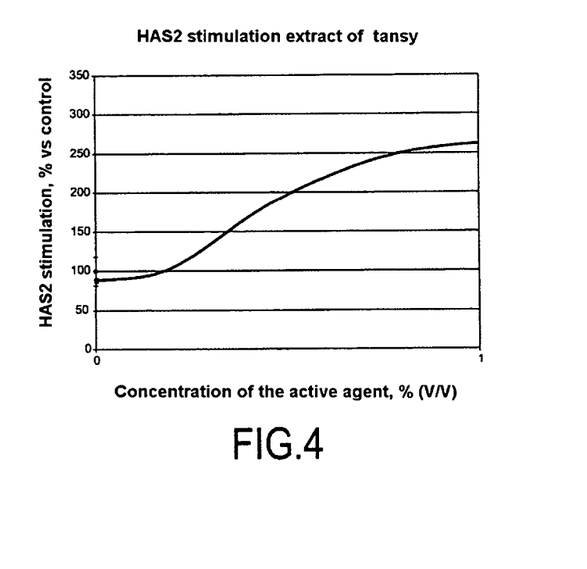
FIG. 4 is a graphical representation of the HAS2 stimulation with an extract of tansy.

Fibroblast cultures are prepared as indicated in Example 1 and are incubated in the presence of increasing amounts of the extract selected (extract of tansy). After mRNA extraction, the amounts of mRNA encoding HAS2 are detected using Q-RT-PCR as described in Example 1. The results are given as percentage activation as a function of the nontreated cell culture, used as a study control, and are given in FIG. 4. A significant dose-effect is observed for this active agent, which means that its activity must be relatively specific. When used at 1%, this extract makes it possible to obtain a 260% stimulation of HAS2 mRNA, which represents a very positive result.

Example 6: Dose-effect Validation of the Effects Obtained with One of the Ingredients Selected (Extract of Indian Shell Flower-JVEG2304A)

Figure 5:
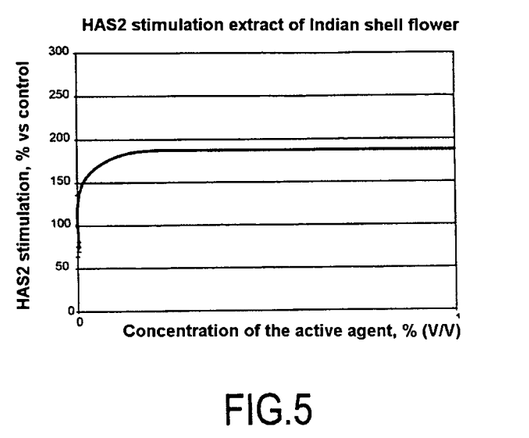
FIG. 5 is a graphical representation of the HAS2 stimulation with an extract of Indian shell flower.

Fibroblast cultures are prepared as indicated in Example 1 and are incubated in the presence of increasing amounts of the extract selected (extract of Indian shell flower). After mRNA extraction, the amounts of mRNA encoding HAS2 are detected using Q-RT-PCR as described in Example 1. The results are given as percentage activation as a function of the nontreated cell culture, used as a study control, and are given in FIG. 5. A significant dose-effect is observed for this active agent, which means that its activity must be relatively specific. When used at 1%, this extract makes it possible to obtain a 180% stimulation of HAS2 mRNA, which represents a very positive result.

Example 7: Cell Culture Tests

The products of the invention extract of *Pentadiplandra brazzeana* (JVEG 060A), extract of Indian shell flower (JVEG 203A), extract of tansy (JVEG 681A) and extract of white mulberry (JVEG 022A) are evaluated for their ability to stimulate the neosynthesis of glycosaminoglycans (GAGs, in particular hyaluronic acid). The biological models selected are the dermis equivalent (DE; free lattices of retracted collagen comprising fibroblasts) and the culture of normal human dermal fibroblasts in monolayer culture (NHDFs).

These effects were evaluated by quantifying the incorporation of tritiated glucosamine into the neosynthesized GAG fraction by the fibroblasts of the models selected. The incorporation of glucosamine into the purified GAG fraction takes account of the neosynthesis of most GAGs, including hyaluronic acid (predominantly). The analysis was carried out separately on the secreted/soluble fractions (secreted GAGs) and on the DE-integrated fractions (GAGs stored in the matrix) or on a whole fibroblast culture (NHDF).

Dermis Equivalents

The dermis equivalents were prepared and then placed in DMEM medium (Invitrogen) containing 2% FCS and left to retract for 7 days with the medium being changed every 3 days. The DEs were subsequently incubated in the presence or absence (control) of the test compounds or of the reference compound (TGF-beta, 10 ng/ml) for 48 hours or 72 hours at 37° C. and 5% $CO_2$ with the addition of tritiated glucosamine 24 hours before the end of the incubation. Each condition was carried out in triplicate.

Fibroblasts

Normal human dermal fibroblasts were seeded in complete DMEM medium and preincubated for 24 hours at 37° C. and 5% $CO_2$, and the culture medium was then replaced with DMEM medium with 2% serum containing or not containing (control) the test compounds or the reference product (TGF-beta, 10 ng/ml). Each experimental condition was carried out in triplicate. The cells were subsequently incubated at 37° C. for 72 hours with the addition of tritiated glucosamine 24 hours before the end of the incubation.

Analysis of Incorporated Radioactivity 24 hours before the end of the incubation, the tritiated glucosamine (D-[6-$^3$H]-glucosamine, 1.37 Tbq/mmol, 37 Ci/mmol, 33 µCi/ml) is added to the culture. The glycosaminoglycan extraction is carried out on the DE culture supernatants (secreted/soluble fraction), within the actual DEs by grinding (extracted fraction), or within the fibroblast culture, using a chaotropic buffer (50 mM Tris/HCl, 4 M guanidine, 5 mM EDTA, pH 8.0). The purification is carried out by ion exchange chromatography: adsorption of the anionic molecules onto Q-sepharose beads under high stringency conditions, desorption of the barely and moderately anionic molecules with 6 M urea plus 0.2 M NaCl, and washing. The counting of the radioactivity incorporated into the very cationic molecules that have remained on the support (predominantly GAGs; eluted with 2 M NaCl) is carried out by liquid scintillation. The results are expressed as percentage variation in glycosaminoglycan synthesis compared with the control. The intergroup comparisons were carried out by analysis of variants (ANOVA) using the Dunnett's test for multiple comparison.

The reference product TGF-beta (10 ng/ml) greatly stimulated the incorporation of glucosamine into the GAG fraction (stimulation by a factor of 4 compared with the control). This result validates the assay.

Under the experimental conditions of this assay, the extract of Indian shell flower (JVEG203A) and the extract of tansy (JVEG681A), tested at 1%, stimulated the incorporation of glucosamine into the fraction of GAGs synthesized by the fibroblast (respectively, 154% and 143% of the nontreated control, $p<0.01$).

TABLE 2

Effects of the various treatments on the incorporation of
$^3$H-glucosamine into the fraction of GAGs synthesized
by human dermal fibroblasts in culture in vitro.

Incorporation of glucosamine - fibroblasts

| Treatment | cpm | sd | n | % Control | p |
|---|---|---|---|---|---|
| Control | 2439 | 171 | 6 | 100 | — |
| TGFβ 10 ng/ml | 9582 | 624 | 6 | 393 | P < 0.01 |
| JVEG 060A 1% | 2606 | 132 | 3 | 107 | P > 0.05 |
| JVEG 203A 1% | 3744 | 465 | 3 | 154 | P < 0.01 |
| JVEG 681A 1% | 3495 | 76 | 3 | 143 | P < 0.01 |
| JVEG 022A 1% | 2116 | 360 | 3 | 87 | P > 0.05 |

Sd: standard deviation; n: number of assays;
Cpm: number of disintegrations per minute (counts per minute);
p: significance evaluated by statistical test.

Soluble Fraction

The reference product TGF-beta greatly stimulated the incorporation of glucosamine into the soluble and secreted GAG fraction of the dermis equivalents (stimulation by a factor of 3 compared with the control). This result validates the assay.

Under the experimental conditions of this assay, the products extract of tansy (JVEG681A) and extract of white mulberry (JVEG022A), tested at 1%, significantly stimulated the incorporation of glucosamine into the soluble and secreted fraction of the dermis equivalents (respectively, 210%, p<0.01 and 149%, p<0.05). The extract of Indian shell flower (JVEG203A) also made it possible to increase the incorporation of glucosamine into the soluble GAG fraction of the DEs (140% of the control).

Extracted Fraction

TGF-beta stimulated the incorporation of glucosamine into the GAG fraction extracted from the dermis equivalents, but more moderately than into the soluble fraction (stimulation by a factor of 1.6 compared with the control). This result validates the assay.

Under the experimental conditions of this assay, the product extract of tansy (JVEG681A), tested at 1%, significantly stimulated the incorporation of glucosamine into the extracted fraction of the dermis equivalents (150% of the control, p<0.01). As for TGF-beta, this stimulation is weaker than in the soluble fraction.

Tables 3 and 4: Effects of the various treatments on the incorporation of glucosamine into the fraction of GAGs synthesized by the fibroblasts of the dermis equivalents (soluble fractions, Table 3 and extracted fractions, Table 4, below).

Incorporation of glucosamine - DE/soluble fraction

| Treatment | cpm | sd | n | % Control | p |
|---|---|---|---|---|---|
| Control | 6746 | 1302 | 3 | 100 | — |
| TGFβ 10 ng/ml | 20813 | 1268 | 3 | 309 | P < 0.01 |
| JVEG 060A 1% | 5872 | 1060 | 3 | 87 | P > 0.05 |
| JVEG 203A 1% | 9453 | 492 | 3 | 140 | P > 0.05 |
| JVEG 681A 1% | 14188 | 1774 | 3 | 210 | P < 0.01 |
| JVEG 022A 1% | 10018 | 643 | 3 | 149 | P < 0.05 |

Incorporation of glucosamine - DE/extracted fraction

| Treatment | cpm | sd | n | % Control | p |
|---|---|---|---|---|---|
| Control | 11350 | 423 | 3 | 100 | — |
| TGFβ 10 ng/ml | 18552 | 3061 | 3 | 163 | P < 0.01 |
| JVEG 060A 1% | 9815 | 690 | 3 | 86 | P > 0.05 |
| JVEG 203A 1% | 10634 | 130 | 3 | 94 | P > 0.05 |
| JVEG 681A 1% | 17069 | 506 | 3 | 150 | P < 0.01 |
| JVEG 022A 1% | 8821 | 1004 | 3 | 78 | P > 0.05 |

Example 8: In Vivo Tests

The objective of this test is to evaluate the effects of the products of the invention on firmness and elasticity, 30 minutes after an isolated application, and also after twice-daily use for 1 month. The effects on the biomechanical properties of the skin are evaluated by means of a ballistometer, a technique which is based on the dynamic recording of the rebound of a heavy object on the surface of the skin.

The rebounds induced, recorded for 3 seconds, are then translated into electrical signals that can be quantified and evaluated in terms of amplitude. The parameters measured are:

indentation (penetration of the probe into the skin for the first impact), which measures the firmness of the skin: if the indentation decreases, there is firming.

the area under the curve measures the energy restored. The latter is effected both by the elasticity and by the firmness of the skin: a decrease in the area corresponds to firming.

alpha, the degree of absorption of the rebounds, which indicates the rate at which the rebounds disappear, related to the elasticity: if alpha increases, the elasticity decreases.

Two formulations (a cream and a serum) were evaluated by twice-daily application over the entire face for one month, under normal conditions of use, each formulation being tested on 20 female volunteers aged 45 to 75. The cream was an O/W emulsion containing 1% of extract of Indian shell flower and 1% of extract of tansy, the serum was an emulsified gel containing 1.5% of extract of Indian shell flower and 1.5% of extract of tansy.

Analysis of the biomechanical properties of the skin showed, on average over all the volunteers, after twice-daily use of the cream or of the serum for one month, a significant decrease in indentation (penetration of the probe into the skin for the first impact) of 12% and 7%, respectively. This observation demonstrates a significant improvement in the firmness of the skin after topical application of the products of the invention. More specifically, for the cream, the following are observed:

an improvement in indentation, measured in 86% of the volunteers, improvement of 16% in the latter (maximum value: −37%), the alpha coefficient significantly increases by 62% and the area under the curve significantly decreases by 32%: these 2 parameters are related to the indentation and therefore confirm the firming effect.

Figure 6:
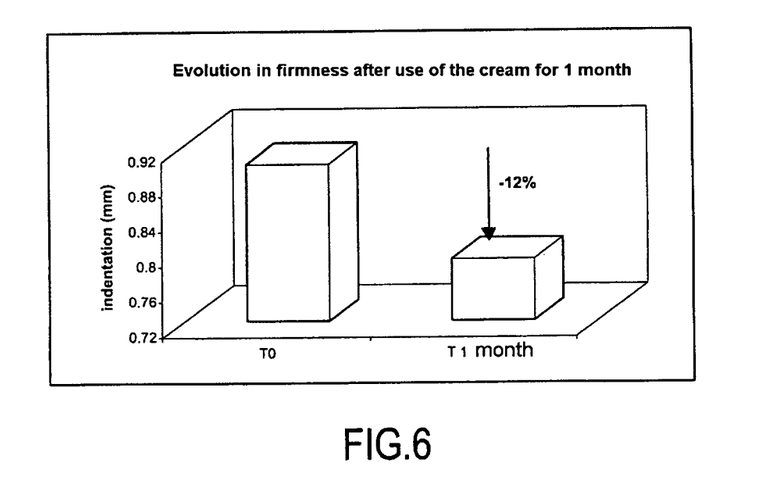
FIG. 6 is a graph of the change in firmness of the skin after one-months use of a cream comprising an extract of Indian shell flower and an extract of tansy.

After twice-daily use of the cream for one month, the skin is significantly firmed by 12%, as illustrated in FIG. 6.

More specifically, for the serum, the following are observed:

an improvement in indentation, measured in 71% of the volunteers, improvement of 13% in the latter (maximum value: −31%), the alpha coefficient significantly increases by 8% and the area under the curve significantly decreases by 18%, also confirming that there is firming of the skin.

Figure 7:
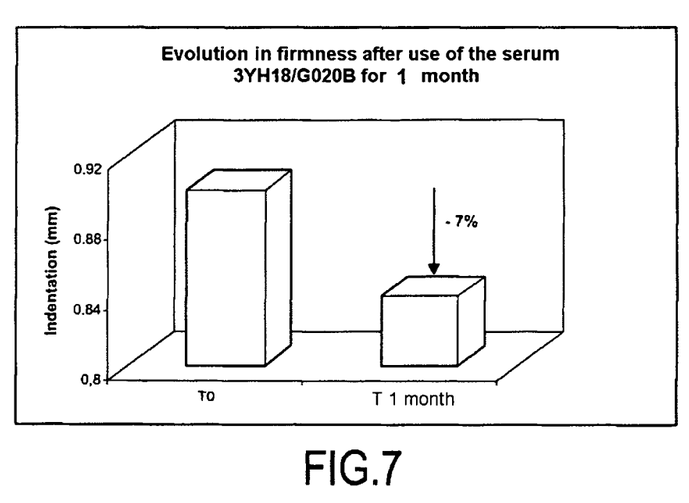
FIG. 7 is a graph of the change of firmness of the skin after one-month's use of a serum comprising an extract of Indian shell flower and an extract of tansy.

After twice-daily use of the serum for one month, the skin is significantly firmed by 7%, as illustrated in FIG. 7.

Example 9: Evaluation of the Absence of Inflammatory Potential of the Molecules Selected for the Stimulation of HAS2 Synthesis Unlike retinoic acid, TNF-alpha and IL1, the molecules selected for stimulating HAS2 synthesis do not involve a pro-inflammatory mechanism which is incompatible with cosmetic applications. Thus, the use of an extract of Indian shell flower under the conditions of Example 6, on fibroblast cultures, makes it possible to stimulate HAS2 while at the same time not stimulating (assay on fibroblast culture supernatant 48 h after contact) the synthesis of pro-inflammatory cytokines known to stimulate HAS2, such as IL1, TNFa or TGFβ (the positive control of Example 6).

TABLE 5

|  | Interleukins | |
|---|---|---|
|  | Control | Indian shell flower |
| Il1a(f5/6) | 1 | 1 |
| Il1b(G5/6) | 1 | 0 |
| Il1-ra(H5/6) | 1.5 | 2 |
| Il2(I5/6) | 0 | 0 |
| Il3(J5/6) | 0 | 0 |
| Il4(K5/6) | 0 | 0 |
| Il5(L5/6) | 0 | 0 |
| Il7(N5/6) | 0 | 1 |
| Il10(B5/6) | 0.5 | 0 |
| Il13(C5/6) | 0 | 0 |
| Il15(D5/6) | 1 | 0 |
| Il16(E5/6) | 0 | 0 |
| IFNg(K3/4) | 0.5 | 0.5 |
| TGF-b1(F9/10) | 1 | 1 |
| TGF-b3(G9/10) | 2.5 | 2.5 |
| TNFa(H9/10) | 1.5 | 2 |
| TNFb(I9/10) | 4.5 | 5.5 |
| BDNF(G1/2) | 4.5 | 5 |
| CNTF(L1/2) | 2.5 | 2.5 |
| GDNF(H3/4) | 1.5 | 1 |
| NT-3(M7/8) | 1.5 | 2.5 |
| Neutrophic factors | | |

Thus, the use of an extract of tansy under the conditions of Example 5, on fibroblast cultures, makes it possible to stimulate HAS2 while at the same time not stimulating (assay on fibroblast culture supernatant 48 h after contact) the synthesis of pro-inflammatory cytokines known to stimulate HAS2, such as IL1, TNFα or TGFβ (the positive control of Example 5).

TABLE 6

|  | Interleukins | |
|---|---|---|
|  | Control | Tansy |
| Il1a(f5/6) | 1 | 0 |
| Il1b(G5/6) | 1 | 1 |
| Il1-ra(H5/6) | 1.5 | 1.5 |
| Il2(I5/6) | 0 | 1 |
| Il3(J5/6) | 0 | 0.5 |
| Il4(K5/6) | 0 | 0.5 |
| Il5(L5/6) | 0 | 0.5 |
| Il7(N5/6) | 0 | 1 |
| Il10(B5/6) | 0.5 | 0.5 |
| Il15(D5/6) | 1 | 0 |
| Il16(E5/6) | 0 | 0 |
| IFNg(K3/4) | 0.5 | 0 |
| TGF-b1(F9/10) | 1 | 1 |
| TGF-b3(G9/10) | 2.5 | 2 |
| TNFa(H9/10) | 1.5 | 1 |
| TNFb(I9/10) | 4.5 | 5 |
| BDNF(G1/2) | 4.5 | 4 |
| CNTF(L1/2) | 2.5 | 1.5 |
| GDNF(H3/4) | 1.5 | 1.5 |
| NT-3(M7/8) | 1.5 | 2 |
| Neutrophic factors | | |

Thus, the use of an extract of lupin under the conditions of Example 1, on fibroblast cultures, makes it possible to stimulate HAS2 while at the same time not stimulating (assay on fibroblast culture supernatant 48 h after contact) the synthesis of pro-inflammatory cytokines known to stimulate HAS2, such as IL1, TNFα or TGFβ (the positive control of Examples 1 to 7).

TABLE 7

|  | Interleukins | |
|---|---|---|
|  | Control | Lupin |
| Il1a(f5/6) | 1 | 0.5 |
| Il1b(G5/6) | 1 | 0 |
| Il1-ra(H5/6) | 1.5 | 0.5 |
| Il2(I5/6) | 0 | 0 |
| Il3(J5/6) | 0 | 0 |
| Il4(K5/6) | 0 | 0 |
| Il5(L5/6) | 0 | 0 |
| Il7(N5/6) | 0 | 0.5 |
| Il10(B5/6) | 0.5 | 0 |
| Il13(C5/6) | 0 | 0 |
| Il15(D5/6) | 1 | 0 |
| Il16(E5/6) | 0 | 0 |
| IFNg(K3/4) | 0.5 | 0.5 |
| TGF-b1(F9/10) | 1 | 1 |
| TGF-b3(G9/10) | 2.5 | 1.5 |
| TNFa(H9/10) | 1.5 | 1 |
| TNFb(I9/10) | 4.5 | 3 |
| BDNF(G1/2) | 4.5 | 4.5 |
| CNTF(L1/2) | 2.5 | 2.5 |
| GDNF(H3/4) | 1.5 | 0.5 |
| NT-3(M7/8) | 1.5 | 1.5 |
| Neutrophic factors | | |

Example 10: Use of the Products of the Invention in Cosmetic or Pharmaceutical Formulations of Oil-in-water Emulsion Type

| Formulation a: O/W emulsion | | |
|---|---|---|
| A | Water | qs 100 |
|  | Butylene glycol | 2 |
|  | Glycerol | 3 |
|  | Sodium dihydroxycetyl phosphate, isopropyl hydroxycetyl ether | 2 |
| B | Glycol stearate SE | 14 |
|  | Triisononaoin | 5 |
|  | Octyl cocoate | 6 |

Formulation a: O/W emulsion

| | | |
|---|---|---|
| C | Butylene glycol, methylparaben, ethylparaben, propylparaben, pH adjusted to 5.5 | 2 |
| D | Products of the invention | 0.01-10% |

Formulation b: O/W emulsion

| | | |
|---|---|---|
| A | Water | qs 100 |
| | Butylene glycol | 2 |
| | Glycerol | 3 |
| | Polyacrylamide, isoparaffin, laureth-7 | 2.8 |
| B | Butylene glycol, methylparaben, ethylparaben, propylparaben; | 2.5 |
| | Phenoxyethanol, methylparaben, propylparaben, butylparaben, ethylparaben | 2 |
| D | Products of the invention | 0.01-10% |

Formulation c: O/W emulsion

| | | |
|---|---|---|
| A | Carbomer | 0.50 |
| | Propylene glycol | 3 |
| | Glycerol | 5 |
| | Water | qs 100 |
| B | Octyl cocoate | 5 |
| | Bisabolol | 0.30 |
| | Dimethicone | 0.30 |
| C | Sodium hydroxide | 1.60 |
| D | Phenoxyethanol, methylparaben, propylparaben, butylparaben, ethylparaben | 0.50 |
| E | Fragrance | 0.30 |
| F | Products of the invention | 0.01-10% |

Example 11: Use of the Products of the Invention in a Formulation of Water-in-oil Type

| | | |
|---|---|---|
| A | PEG-30 dipolyhydroxystearate | 3 |
| | Capric triglycerides | 3 |
| | Cetearyl octanoate | 4 |
| | Dibutyl adipate | 3 |
| | Grape seed oil | 1.5 |
| | Jojoba oil | 1.5 |
| | Phenoxyethanol, methylparaben, propylparaben, butylparaben, ethylparaben | 0.5 |
| B | Glycerol | 3 |
| | Butylene glycol | 3 |
| | Magnesium sulphate | 0.5 |
| | EDTA | 0.05 |
| | Water | qs 100 |
| C | Cyclomethicone | 1 |
| | Dimethicone | 1 |
| D | Fragrance | 0.3 |
| E | Product of the invention | 0.01-10% |

Example 12: Use of the Products of the Invention in a Formulation of Shampoo or Shower Gel Type

| | | |
|---|---|---|
| A | Xantham gum | 0.8 |
| | Water | qs 100 |
| B | Butylene glycol, methylparaben, ethylparaben, propylparaben | 0.5 |
| | Phenoxyethanol, methylparaben, propylparaben, butylparaben, ethylparaben | 0.5 |
| C | Citric acid | 0.8 |
| D | Sodium laureth sulphate | 40.0 |
| E | Product of the invention | 0.01-10% |

Example 13: Use of the Products of the Invention in a Formulation of Lipstick Type and Other Anhydrous Products

| | | |
|---|---|---|
| A | Mineral wax | 17.0 |
| | Isostearyl isostearate | 31.5 |
| | Propylene glycol dipelargonate | 2.6 |
| | Propylene glycol isostearate | 1.7 |
| | PEG-8 beeswax | 3.0 |
| | Hydrogenated palm kernel oil glycerides, Hydrogenated palm glycerides | 3.4 |
| | Lanolin oil | 3.4 |
| | Sesame oil | 1.7 |
| | Cetyl lactate | 1.7 |
| | Mineral oil, lanolin alcohol | 3.0 |
| B | Castor oil | qs 100 |
| | Titanium dioxide | 3.9 |
| | CI 15850:1 | 0.616 |
| | CI 45410:1 | 0.256 |
| | CI 19140:1 | 0.048 |
| | CI 77491 | 2.048 |
| C | Product of the invention | 0.01-5% |

Example 14: Use of the Products of the Invention in an Aqueous Gel Formulation (Area Around the Eyes, Slimming, Etc.)

| | | |
|---|---|---|
| A | Water | qs 100 |
| | Carbomer | 0.5 |
| | Butylene glycol | 15 |
| | Phenoxyethanol, methylparaben, propylparaben, butylparaben, ethylparaben | 0.5 |
| B | Products of the invention | 0.01-10% |

The invention claimed is:

1. A method of cosmetic care for combating the effects of aging on the skin or the loss of firmness of the skin observed in the course of aging by stimulating the expression and/or the activity of hyaluronan synthase 2 (HAS2) in fibroblast cells of cutaneous tissue in a human in need thereof, said method comprising the step of topically applying to facial cutaneous tissue of a human in need thereof an effective amount of a stimulating agent, said stimulating agent being in a composition, and said stimulating agent being an Indian shell flower leaves extract (*Alpinia galanga*) which is an aqueous fraction obtained by extraction in water with (i) agitation without heating; (ii) heating at a temperature between 30 and 60° C.; or (iii) both agitation and heating at a temperature between 30 and 60° C., and the composition comprising a dermatologically-acceptable carrier.

2. The method according to claim 1, wherein the effective amount of the Indian shell flower leaves extract (*Alpinia galanga*) is an amount between 0.001% and 20% by weight of the total composition.

3. A method of cosmetic care for improving in the skin, firmness and/or elasticity and/or tissue moisturization, and/or increasing the skin barrier effect, and/or increasing tissue resilience, and/or improving cell proliferation, migration or differentiation by stimulating the expression and/or the activity of hyaluronan synthase 2 (HAS2) in fibroblast cells of cutaneous tissue in a human in need thereof, said method comprising the step of topically applying to facial cutaneous tissue of a human in need thereof an effective amount of a stimulating agent, said stimulating agent being in a composition, and said stimulating agent being an Indian shell flower leaves extract (*Alpinia galanga*) which is an aqueous fraction obtained by extraction in water with (i) agitation without heating; (ii) heating at a temperature between 30 and 60° C.; or (iii) both agitation and heating at a temperature between 30 and 60° C., and the composition comprising a dermatologically-acceptable carrier.

4. The method of claim 1, wherein the facial, cutaneous tissue of a human in need thereof onto which the Indian shell flower leaves extract (*Alpinia galanga*) in the composition is applied are facial cutaneous tissue containing normal dermal fibroblast.

5. The method of claim 3, wherein the facial cutaneous tissue of a human in need thereof onto which the Indian shell flower leaves extract (*Alpinia galanga*) in the composition is applied are facial cutaneous tissue containing normal dermal fibroblast.

6. The method of claim 3, wherein the effective amount of the Indian shell flower leaves extract (*Alpinia galanga*) is an amount between 0.001% and 20% by weight of the total composition.

7. A method of cosmetic care for combating the effects of aging on the skin or the loss of firmness of the skin observed in the course of aging by stimulating the expression and/or the activity of hyaluronan synthase 2 (HAS2) in fibroblast cells of cutaneous tissue in a human in need thereof, said method comprising the step of topically applying to facial cutaneous tissue of a human in need thereof an effective amount of a composition comprising:
(a) an effective amount of a stimulating agent, said stimulating agent comprising a plant extract consisting of:
(1) an Indian shell flower leaves extract (*Alpinia galanga*), or
(2) an Indian shell flower leaves extract (*Alpinia galanga*) and at least one plant extract selected from the group consisting of an extract of Guarana (*Paullinia cupana*), an extract of Ephedra (*Ephedra sinica*), an extract of tansy (*Tanacetum vulgare*), an extract of white mulberry (*Morus alba*), an extract of J'oublie (*Pentadiplandra brazzeana*), an extract of Indian shell flower roots (*Alpinia galanga*), an extract of St. John's wort (*Hypericum hircinum*), an extract of bamboo (*Bambusa vulgaris*), an extract of mung bean (*Phaseolus aureus*), an extract of gooseberry (*Ribes* uva-*crispa* L.), an extract of butcher's broom (*Ruscus aculeatus*), an extract of broad bean (*Vicia faba equina*), an extract of pea (*Pisum sativum*), an extract of lupin (*Lupinus angustifolius*), plant oils, jojoba oil, plant esters, grapeseed oil, sesame oil, hydrogenated palm-kernel oil, hydrogenated palm oil glyceride, essential oils, clove oils, camphor, eucalyptus oils, witch hazel distillate, aloe vera, and mixtures thereof,
wherein the Indian shell flower leaves extract (*Alpinia galanga*) is the an aqueous fraction obtained by extraction in water with (i) agitation without heating; (ii) heating at a temperature between 30 and 60° C.; or (iii) both agitation and heating at a temperature between 30 and 60° C., and
(b) a dermatologically-acceptable carrier.

8. The method according to claim 7, wherein the effective amount of the Indian shell flower leaves extract (*Alpinia galanga*) is an amount between 0.001% and 20% by weight of the total composition.

9. The method of claim 7, wherein the facial cutaneous tissue of a human in need thereof onto which the composition is applied are facial cutaneous tissue containing normal dermal fibroblast.

10. A method of cosmetic care for improving in the skin, firmness and/or elasticity and/or tissue moisturization, and/or increasing the skin barrier effect, and/or increasing tissue resilience, and/or improving cell proliferation, migration or differentiation by stimulating the expression and/or the activity of hyaluronan synthase 2 (HAS2) in fibroblast cells of cutaneous tissue in a human in need thereof, said method comprising the step of topically applying to facial cutaneous tissue of a human in need thereof an effective amount of a composition comprising:
(a) an effective amount of a stimulating agent, said stimulating agent comprising a plant extract consisting of:
(1) an Indian shell flower leaves extract (*Alpinia galanga*), or
(2) an Indian shell flower leaves extract (*Alpinia galanga*) and at least one plant extract selected from the group consisting of an extract of Guarana (*Paullinia cupana*), an extract of Ephedra (*Ephedra sinica*), an extract of tansy (*Tanacetum vulgare*), an extract of white mulberry (*Morus alba*), an extract of J'oublie (*Pentadiplandra brazzeana*), an extract of Indian shell flower roots (*Alpinia galanga*), an extract of St. John's wort (*Hypericum hircinum*), an extract of bamboo (*Bambusa vulgaris*), an extract of mung bean (*Phaseolus aureus*), an extract of gooseberry (*Ribes* uva-*crispa* L.), an extract of butcher's broom (*Ruscus aculeatus*), an extract of broad bean (*Vicia faba equina*), an extract of pea (*Pisum sativum*), an extract of lupin (*Lupinus angustifolius*), plant oils, jojoba oil, plant esters, grapeseed oil, sesame oil, hydrogenated palm-kernel oil, hydrogenated palm oil glyceride, essential oils, clove oils, camphor, eucalyptus oils, witch hazel distillate, aloe vera, and mixtures thereof,
wherein the Indian shell flower leaves extract (*Alpinia galanga*) is an aqueous fraction obtained by extraction in water with (i) agitation without heating; (ii) heating at a temperature between 31) and 60° C.; or (iii) both agitation and heating at a temperature between 30 and 60° C., and
(b) a dermatologically-acceptable carrier.

11. The method according to claim 10, wherein the effective amount of the Indian shell flower leaves extract (*Alpinia galanga*) is an amount between 0.001% and 20% by weight of the total composition.

12. The method of claim 10, wherein the facial cutaneous tissue of a human in need thereof onto which the composition is applied are facial cutaneous tissue containing normal dermal fibroblast.

* * * * *